US011291421B2

(12) United States Patent
Radicke et al.

(10) Patent No.: US 11,291,421 B2
(45) Date of Patent: Apr. 5, 2022

(54) METHOD FOR DETERMINING ORTHOGONAL SLICE IMAGE DATA SETS OF A TOMOSYNTHESIS RECORDING

(71) Applicant: Siemens Healthcare GmbH, Erlangen (DE)

(72) Inventors: Marcus Radicke, Veitsbronn (DE); Stefan Veitenhansl, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 13 days.

(21) Appl. No.: 17/030,538

(22) Filed: Sep. 24, 2020

(65) Prior Publication Data

US 2021/0093276 A1  Apr. 1, 2021

(30) Foreign Application Priority Data

Sep. 30, 2019  (EP) .................................... 19200379
Sep. 11, 2020  (EP) .................................... 20195667

(51) Int. Cl.
  *G06T 11/00* (2006.01)
  *H04N 1/60* (2006.01)
  (Continued)

(52) U.S. Cl.
  CPC .............. *A61B 6/502* (2013.01); *A61B 6/025* (2013.01); *A61B 6/12* (2013.01); *A61B 6/461* (2013.01);
  (Continued)

(58) Field of Classification Search
  CPC ........... G06T 2211/424; G06T 2200/24; G06T 2211/436; G06T 2207/10112;
  (Continued)

(56) References Cited

U.S. PATENT DOCUMENTS 9,053,565 B2   6/2015  Buelow et al.
2008/0187095 A1  8/2008  Boone et al.
(Continued)

FOREIGN PATENT DOCUMENTS

DE   102012200207 B3   5/2013

OTHER PUBLICATIONS

Waldherr, Christian et al:; "Tomosynthesis-guided vacuum-assisted breast biopsy: A feasibility study"; European Radiology; Springer International, Berlin; vol. 26; No. 6; pp. 1582-1589; XP035874347; ISSN: 0938-7994; DOI: 10.1007/S00330-015-4009-4; 2015.
(Continued)

*Primary Examiner* — Don K Wong
(74) *Attorney, Agent, or Firm* — Harness, Dickey & Pierce, P.L.C.

(57) ABSTRACT

A method is for determining orthogonal slice image data sets of a tomosynthesis recording of an examination region. In an embodiment, the method includes recording a tomosynthesis recording and reconstructing a plurality of first slice image data sets in a first plane based upon the tomosynthesis recording; selecting a first slice image data set from the plurality of first slice image data sets; marking a microcalcification or a region of interest with a punctiform marking in the first slice image data set selected; and determining, from a second slice image data set in a second plane orthogonal to the first plane, and from a third slice image data set in a third plane orthogonal to the first plane and the second plane, wherein a point of intersection of the first plane, the second plane and the third plane includes the punctiform marking.

20 Claims, 4 Drawing Sheets

(51) Int. Cl.
*G09G 5/02* (2006.01)
*A61B 6/00* (2006.01)
*A61B 6/02* (2006.01)
*A61B 6/12* (2006.01)
*G06K 9/62* (2022.01)

(52) U.S. Cl.
CPC ............ *A61B 6/468* (2013.01); *A61B 6/5211* (2013.01); *A61B 6/54* (2013.01); *G06K 9/6218* (2013.01)

(58) Field of Classification Search
CPC . G06T 2207/30068; G06T 2207/30196; G06T 2210/41; G09G 5/02; G09G 2300/0452; A61B 6/502; A61B 6/032; A61B 6/5205; H04N 1/6027
See application file for complete search history.

(56) References Cited

U.S. PATENT DOCUMENTS

2015/0279064 A1* 10/2015 Dennerlein .............. G09G 5/02
382/131
2016/0217568 A1 7/2016 Vancamberg et al.

OTHER PUBLICATIONS

Extended European Search Report dated Feb. 23, 2021.

\* cited by examiner

METHOD FOR DETERMINING ORTHOGONAL SLICE IMAGE DATA SETS OF A TOMOSYNTHESIS RECORDING

PRIORITY STATEMENT

The present application hereby claims priority under 35 U.S.C. § 119 to European patent applications numbers EP 20195667.9 filed Sep. 11, 2020 and EP 19200379.6 filed Sep. 30, 2019, the entire contents of each of which are hereby incorporated herein by reference.

FIELD

Embodiments of the invention generally relate to a method for determining orthogonal slice image data sets of a tomosynthesis recording of an examination region, a mammography system, a computer program product and a computer-readable medium for this purpose.

BACKGROUND

In breast imaging, in particular, in the context of screening and diagnostics, breast tomosynthesis is becoming ever more accepted and may be becoming established as a standard. This transition from a 2D modality, for example, of digital full-field mammography to a 3D modality of breast tomosynthesis can involve some challenges in everyday clinical practice. In the context of the invention, the challenge of the time-effective reading of the data and the optimization of the biopsy process are considered. The inventors have discovered that it would be desirable if the radiologist did not have to assess all the reconstructed tomosynthesis slices, but could make a diagnosis or identify a suspect biopsy region based upon a single image.

For example, a synthetic mammogram is known in which a two-dimensional image is calculated from the three-dimensional data. The disadvantage of this synthetic mammogram is that it is, in part, not apparent to the radiologist whether a local microcalcification accumulation visible in the two-dimensional image is actually a local cluster or whether the microcalcifications are distributed over the breast depth which is not representable in the two-dimensional image and therefore whether an increased likelihood of malignancy exists.

A further challenge regarding the representation arises in the biopsy workflow. Here too, calcification clusters cannot be recognized in their spatial extent at a glance. In a tomo-biopsy, the radiologist must scroll through a plurality of slices and estimate the center of the calcification cluster. In stereo-biopsy, two views are provided, although the angles are effectively too small to be able to ascertain a complete spatial extent reliably. Until now, it has not yet been possible to achieve the desired accuracy in the determination of the center of the cluster. For example, until now it has been commonplace, by way of dynamic observation of a plurality of parallel or mutually inclined slices, to obtain an estimate of the depth distribution of the microcalcifications.

SUMMARY

In particular, the inventors have discovered that during the setting and marking of the target for the biopsy, a further visual assistance would be useful and desirable. In addition, there is a lack of visual information as to whether the size of the notch is sufficient for the corresponding extent of the calcification cluster.

Embodiments of the invention provide a method for determining orthogonal slice image data sets of a tomosynthesis recording of an examination region, a mammography system, a computer program product and a computer-readable medium, which enable an improved localization of a microcalcification or of a cluster.

Embodiments are directed to a method for determining orthogonal slice image data sets of a tomosynthesis recording of an examination region; a mammography system; a computer program product; and a computer-readable medium.

At least one embodiment of the invention relates to a method for determining orthogonal slice image data sets of a tomosynthesis recording of an examination region, in particular, a breast, having the steps of recording, reconstructing, selecting, masking and determining. In the step of recording, a tomosynthesis recording is made. In the step of reconstructing, a plurality of first slice image data sets is reconstructed in a first plane based upon the tomosynthesis recording. In the step of selecting, a first slice image data set is selected from the plurality of first slice image data sets. In the step of marking, a microcalcification or a region of interest is marked with a punctiform marking in the selected first slice image data set. In the step of determining, a second slice image data set is determined in a second plane orthogonal to the first plane and a third slice image data set is determined in a third plane orthogonal to the first plane and the second plane, wherein the point of intersection of the first plane, the second plane and the third plane includes the punctiform marking.

At least one embodiment of the invention further relates to a mammography system having devices for carrying out a method according to at least one embodiment of the invention. The mammography system can have, in particular, a biopsy unit. The mammography system has a recording unit for making the tomosynthesis recording. The recording unit can comprise, in particular, the X-ray source and the X-ray detector. The mammography system has a reconstruction unit for reconstructing a volume image or from a plurality of first slice images. The reconstruction unit can be included by the computer unit. The mammography system further has a selection unit for selecting a first slice image data set from the plurality of first slice image data sets. The mammography system further has a marking unit for marking a microcalcification or a region of interest with a punctiform marking in the selected first slice image data set. The selecting unit and the marking unit can comprise a, possibly common, input unit. The mammography system further has a determining unit for determining from a second slice image data set in a second plane orthogonal to the first plane and from a third slice image data set in a third plane orthogonal to the first plane and the second plane, wherein the point of intersection of the first plane, the second plane and the third plane includes the punctiform marking.

At least one embodiment of the invention further relates to a computer program product with a computer program which can be loaded directly into a memory apparatus of a control apparatus of a mammography system, having program portions in order to carry out all the steps of a method according to at least one embodiment of the invention when the computer program is executed in the control device of the mammography system.

At least one embodiment of the invention further relates to a computer-readable medium on which program portions that are configured to be read in and executed by a computer unit are stored, in order to carry out all the steps of a method according to at least one embodiment of the invention when the program portions are executed by the mammography system.

At least one embodiment of the invention further relates to a method for determining orthogonal slice image data sets of a tomosynthesis recording of an examination region, the method comprising:

recording a tomosynthesis recording and reconstructing a plurality of first slice image data sets in a first plane based upon the tomosynthesis recording;

selecting a first slice image data set from the plurality of first slice image data sets;

marking a microcalcification or a region of interest with a punctiform marking in the first slice image data set selected; and determining, from a second slice image data set in a second plane orthogonal to the first plane, and from a third slice image data set in a third plane orthogonal to the first plane and the second plane, wherein a point of intersection of the first plane, the second plane and the third plane includes the punctiform marking.

At least one embodiment of the invention further relates to a non-transitory computer program product storing a computer program, directly loadable into a memory apparatus of a control apparatus of a mammography system, including program portions to carry out the method of claim 1 when the computer program is executed in the control apparatus of the mammography system.

At least one embodiment of the invention further relates to a non-transitory computer-readable medium storing program portions, configured to be read in and executed by a computer unit, to carry out the method of claim 1 when the program portions are executed by the mammography system.

BRIEF DESCRIPTION OF THE DRAWINGS

Example embodiments of the invention will now be described in more detail, making reference to the drawings. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for determining orthogonal slice image data sets of a tomosynthesis recording of an examination region, in particular, a breast, having the steps of recording, reconstructing, selecting, masking and determining. In the step of recording, a tomosynthesis recording is made. In the step of reconstructing, a plurality of first slice image data sets is reconstructed in a first plane based upon the tomosynthesis recording. In the step of selecting, a first slice image data set is selected from the plurality of first slice image data sets. In the step of marking, a microcalcification or a region of interest is marked with a punctiform marking in the selected first slice image data set. In the step of determining, a second slice image data set is determined in a second plane orthogonal to the first plane and a third slice image data set is determined in a third plane orthogonal to the first plane and the second plane, wherein the point of intersection of the first plane, the second plane and the third plane includes the punctiform marking.

In the tomosynthesis recording in at least one embodiment, in the step of recording, a plurality of projections is typically recorded at different angles in a pre-determined angular region of a breast. From the projections, with the aid of a tomosynthesis reconstruction, in the step of reconstruction, a plurality of first slice image data sets can be reconstructed in a first plane. Thereby, a tomosynthesis volume can be reconstructed from the tomosynthesis recording. The first plane can be, for example, an xy-plane. In the plurality of first slice image data sets, both the glandular tissue and/or the soft tissue as well as—where present—more strongly attenuating microcalcifications can be represented. The expression microcalcification can be shortened to microcalc.

A microcalcification can be identified by an ser or with the aid of an image recognition algorithm. In the step of selecting, for example, a first slice image data set can be selected by the user. Alternatively, the first slice image data set can be selected by an algorithm, for example, for image or pattern recognition. The first slice image data set is selected, in particular, when a microcalcification has been identified in the first slice image data set. The region of interest can be a lesion without microcalcifications which is to be investigated by way of a biopsy.

The microcalcification can be marked, in particular, substantially in a punctiform manner during the step of marking. The marking can be made, for example, with a click or a touch gesture on the user interface which displays the first slice image data set. The microcalcification can be marked automatically as soon as it is identified, for example, by an algorithm. The display can show, for example, the first slice image data set with the marked microcalcification. Now a second and a third slice image data set are generated. The selected first slice image data set and the second and the third slice image data set can be designated orthogonal projections based upon the tomosynthesis data.

It is proposed to provide a representation of a plurality of views with a quasi-static representation in the breast assessment and in the biopsy workflow. In each of the three views or the first, second and third slice image data set, an orthogonal projection from the tomosynthesis data can be represented. The main view can have, in particular, the first slice image data set of the tomosynthesis data set, for example, in the xy-plane. The two other views or the second and third slice image data sets can be designated orthogonal projections starting from the marking. The marking in the (selected) first slice image data set includes the intersection point of a horizontal slice, for example, in the xz-plane and a vertical slice, for example, in the yz-plane. The horizontal slice or the second slice image data set can be formed in the xz-plane. The vertical slice or the third slice image data set can be formed in the yz-plane. The xy, xz and yz planes can be orthogonal planes of the reconstructed tomosynthesis volume based upon the tomosynthesis recording.

The selected first slice image data set can be, in particular, a slice image data set from the stack with the plurality of first slice image data sets or the reconstructed volume of the reconstructed tomosynthesis recording. In the second slice image data set, in particular, the image values of a constant y-value corresponding to the y-coordinate of the punctiform marking dependent upon x and the slice z from the plurality of first slice image data sets can be entered. In the third slice image data set, in particular, the image values of a constant x-value corresponding to the x-coordinate of the punctiform marking dependent upon y and the slice z from the plurality of first slice image data sets can be entered.

Alternatively, another orientation of the second and the third slice image data set can be selected. For example, the second and the third slice image data set can each be oriented rotated at an angle of, for example 45 degrees. This can be advantageous, in particular, with regard to a biopsy path or a trajectory for the biopsy along the angle.

By this, the radiologist or the user receives a direct overview of whether the microcalc accumulation or cluster is locally cohesive in the selected first slice image data set. Advantageously, the assessment can be made clearer and simpler with just one view of the simultaneously represented three views, the selected first slice image data set and the second and third slice image data set. Advantageously, a representation of the orthogonal planes of the 3D volume based upon the tomosynthesis recording can be provided.

In a further optional step of the renewed marking, in particular, the user can click on a particular or known further microcalcification in the first, second or third slice image data set or can select this microcalcification. In a step of emphasizing, the marked further microcalcification can be emphasized in the first, second and third slice image data set, for example, via a circular border. Advantageously, the position of the further microcalcification in the vicinity of the marked microcalcification can be more exactly localized.

Advantageously, the workflow for diagnosis can be accelerated relative to a workflow based upon FFDM recordings. Advantageously, a more intuitive representation with improved possibilities can be provided for more accurate localization of microcalcifications. The position of the adjacent microcalcifications can advantageously be determined more accurately. Advantageously, an improved diagnosis quality can be enabled. Advantageously, sample taking in the biopsy can be carried out more accurately and completely.

According to one embodiment of the invention, at least one microcalcification is detected automatically.

Advantageously, a known algorithm can be used which can detect or identify microcalcifications in the tomosynthesis slices, i.e. the first slice image data sets or the stereotactic images. Advantageously, a list with known microcalcifications can be created. Advantageously, the known microcalcifications can be shown, in particular, to the user in a sequence or, for example, in the list, for selection. Regions with at least one detected microcalcification can be classified as suspect regions. The first, second and third slice image data set can be represented sequentially for different detected microcalcifications, for example, the user can jump to the representation with the next detected and marked microcalcification or the representations can be displayed one after another automatically.

According to one embodiment of the invention, given a plurality of detected microcalcifications, an automatic cluster analysis is carried out. The automatic cluster analysis can be a development of the algorithm for recognizing microcalcifications. Alternatively, the microcalcifications can be detected manually by the user.

The distribution of the known microcalcifications can be evaluated automatically. In the case of the automatic evaluation, the detected microcalcifications can be evaluated with regard to whether a plurality of microcalcifications form a microcalc accumulation or a cluster. For this purpose, the spacing of at least two detected microcalcifications can be evaluated. If the spacing falls below a pre-determined threshold value, the at least two detected microcalcifications are assigned to a cluster. In the selected first, second and third slice image data set, a virtual envelope or border can be overlaid on the cluster boundaries round the associated microcalcifications. Advantageously, clusters can be localized particularly rapidly and easily in the three views. Advantageously, a diagnosis and also a biopsy planning can be improved.

According to one embodiment of the invention, the second slice image data set and the third slice image data set exclusively have the attenuation information of the at least one microcalcification. The orthogonal projections from the tomosynthesis data in the form of the second and third slice image data set have, in particular, substantially only the detected microcalcifications without the breast background. Since the object lies in detecting microclusters, in one example embodiment, based upon the easier detection or identifiability, the second and the third slice image data record can be filled substantially only with microcalcifications and the entire breast background can be not displayed. The second and third slice image data set can be filled, in particular, substantially only with the detected microcalcifications. Advantageously, the position of a plurality of microcalcifications relative to one another can be determined and/or localized particularly easily in a clear representation.

According to one embodiment of the invention, the second slice image data set and the third slice image data set have exclusively the attenuation information of the glandular tissue or the soft tissue, or the attenuation information of the glandular tissue and the at least one calcification. The orthogonal projections of the tomosynthesis recording in the form of the second and third slice image data set have substantially only glandular tissue, in particular, so-called masses and possibly microcalcifications.

Advantageously, potential tumor tissue can be displayed in the second and third slice images. In particular, the combination of microcalcifications and masses in one view can advantageously be used for the diagnosis. In particular, in the case of few detected microcalcifications in the plurality of first slice images or in the selected first slice image data set, the second and the third slice image data set can have the attenuation information of the soft tissue or of the breast background. In an example embodiment, in particular, for the biopsy of lesions without any existing microcalcifications or with very few microcalcifications, the soft tissue can (also) be represented in the corresponding slice images.

In one embodiment, alternatively or additionally to the detected microcalcifications, substantially all the structures represented in the breast can be included by the second and third slice image data set. In one embodiment, alternatively or additionally, substantially only the glandular tissue, in particular, incorporating potential tumors can be included by the second and third slice image data set.

According to one embodiment of the invention, the first slice image data set has the entire attenuation information. The selected first slice image data set comprises substantially all the representable attenuation information of the examination object for this slice, i.e. both the detected microcalcifications and also the soft tissue can be represented. Advantageously, the selected first slice image data set can comprise an overall image of the attenuation information of the object. Advantageously, in the diagnosis both the information relating to masses and also microcalcifications can be obtained at a glance from the selected first slice image data set. The details regarding the extent of lesions or masses and microcalcification clusters can be provided, in particular, by the second and third slice image data set.

According to one embodiment of the invention, the marked microcalcification can be emphasized in the first, second and third slice image data set. A selected microcalcification or a region of interest can be emphasized in the first, second and/or third slice image data set, for example, by way of a colored marking. Advantageously, the microcalcification and its localization can be observed in different views.

According to one embodiment of the invention, the second and third slice image data set has a maximum slice thickness of substantially 4 cm. By way of a key combination and a click on the marked microcalcification or another pre-determined user input in relation to the marked microcalcification based upon the selected first slice image data set, in the second and third slice image data set, just a narrow region of the projection, for example, +/−2 cm can be represented. Alternatively, the narrower region can lie between +/−1 cm and +/−3 cm. Advantageously, adjacent microcalcifications lying in front or behind thereof can be masked out. This can have the advantage, in particular, that in a breast with a large number of microcalcifications, they are not overlaid in the relevant region.

According to one embodiment of the invention, a biopsy region is marked in the first, second and/or third slice image data set. The biopsy region can contain a cluster. The biopsy region can have an additional envelope around the cluster which maintains a pre-defined spacing from the cluster, so that the cluster can be biopsied as reliably as possible. The biopsy region can be carried out manually or automatically, for example, based upon the cluster analysis. A tissue region that is to be biopsied, i.e. a biopsy region, can be selected and marked.

A biopsy region can be selected and marked in place of a target point for the biopsy. The biopsy region can be selectable and markable, in particular, in two or three planes. For example, the biopsy region can be selected and marked in the selected first slice image data set and in the second and/or third slice image data set. Advantageously, during the marking of the biopsy region, the improved localization of the microcalcifications can be taken into account.

According to one embodiment of the invention, a virtual overlaying of a model of a selected biopsy needle with a removal opening, a so-called notch, at least in the first slice image data set is displayed in the marked biopsy region. The model of the biopsy needle can be made available as a three-dimensional model for the overlaying, so that the biopsy needle can be shown in the selected first, in the second and in the third slice image data set. Different available models of biopsy needles, in particular, with a so-called notch can be selectable for virtual overlaying. The selected biopsy needle has a removal opening, the so-called notch. The removal opening can be configured as a lateral vacuum removal window in the biopsy needle. The biopsy can suck in the biopsy material and/or the suspect tissue by rotation.

Advantageously, all the usable needle types and notches can be retrievable as 3D models in the software. These 3D models can be projected or virtually overlaid on an existing image data set. For a biopsy workflow, in addition to the existing slice image data, in particular, in the selected first, second and third slice image data, a virtual overlaying of the selected needle and notch in the slice image data, in particular, in the selected first, second and third slice image data, can be inserted in the selected target position or biopsy region. Herein, the position, alignment and size ratio of the tissue to be biopsied and of the notch are of particular significance, i.e. the virtual overlaying can have, in particular, a size relationship of the slice image data and the needle or notch that is true to the original. This permits the user to determine whether the correct needle thickness, notch size and the correct or optimal access route or path of the needle through the surrounding tissue are selected or proposed. A correction of the biopsy needle, needle thickness, notch size and path would advantageously be possible at this time point since the real biopsy needle has not yet been introduced into the tissue. Advantageously, the second and the third slice image data set can simplify a biopsy planning.

According to one embodiment of the invention, a message is output if the selected biopsy needle incompletely captures the marked biopsy region and/or, for the marked biopsy region, a proposal of a suitable biopsy needle and/or of a biopsy angle is output. An algorithm for planning the biopsy can calculate, based upon the position and extent of the suspect region or of the biopsy region, a recommendation for biopsy needle and notch as well as the optimum access or path or angle and this can subsequently be visualized on the display. Advantageously, the biopsy planning can be improved. Advantageously, a message or an indication can be output if the user wishes to use or has selected a biopsy needle that is unsuitable from the standpoint of the algorithm or an unsuitable notch or an unsuitable access route.

According to one embodiment of the invention, a trajectory for automatic biopsy control of the biopsy needle is calculated. A trajectory or a path for biopsy control based upon the marked biopsy region can be calculated. In particular, an optimum biopsy angle can be determined. The calculation of the biopsy angle can comprise, apart from the optimum angle for positioning the notch on or in the biopsy region, a suitable entry path or a suitable entry site into the breast. Based upon the calculation, the biopsy system can subsequently be controlled automatically, so that a biopsy unit is moved with the biopsy needle to the correct position, possibly after confirmation by the user. The trajectory can be controlled by control signals based upon the calculation. Advantageously, the biopsy can be carried out more accurately. During the calculation or for its visualization, in particular, the second and the third slice image data set can be determined according to the optimum angle relative to the x-axis and the y-axis. The slice image data set can then be determined along an axis which is tilted through the angle relative to the x-axis or the y-axis. Advantageously, the optimum angle for the trajectory can be determined with the aid of the determination of different second and third slice image data sets with different angles.

At least one embodiment of the invention further relates to a mammography system having devices for carrying out a method according to at least one embodiment of the invention. The mammography system can have, in particular, a biopsy unit. The mammography system has a recording unit for making the tomosynthesis recording. The recording unit can comprise, in particular, the X-ray source and the X-ray detector. The mammography system has a reconstruction unit for reconstructing a volume image or from a plurality of first slice images. The reconstruction unit can be included by the computer unit. The mammography system further has a selection unit for selecting a first slice image data set from the plurality of first slice image data sets. The mammography system further has a marking unit for marking a microcalcification or a region of interest with a punctiform marking in the selected first slice image data set. The selecting unit and the marking unit can comprise a, possibly common, input unit. The mammography system further has a determining unit for determining from a second slice image data set in a second plane orthogonal to the first plane and from a third slice image data set in a third plane orthogonal to the first plane and the second plane, wherein the point of intersection of the first plane, the second plane and the third plane includes the punctiform marking.

The advantages of the method according to embodiments of the invention can advantageously be transferred to the mammography system. The mammography system can preferably have a local or a remote display unit for displaying the selected first, second and third slice image data set.

At least one embodiment of the invention further relates to a computer program product with a computer program which can be loaded directly into a memory apparatus of a control apparatus of a mammography system, having program portions in order to carry out all the steps of a method according to at least one embodiment of the invention when the computer program is executed in the control device of the mammography system.

At least one embodiment of the invention further relates to a computer-readable medium on which program portions that are configured to be read in and executed by a computer unit are stored, in order to carry out all the steps of a method according to at least one embodiment of the invention when the program portions are executed by the mammography system.

Figure 1:
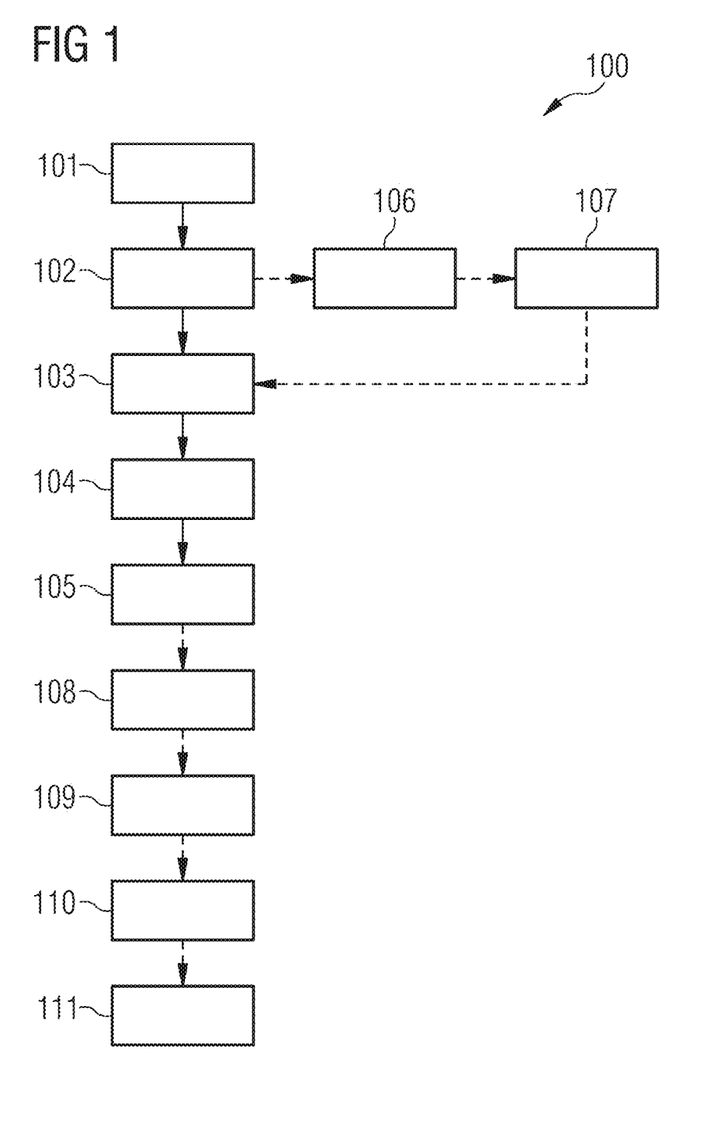
FIG. 1 shows a schematic representation of the method according to an embodiment of the invention.

FIG. 1 shows an example embodiment of the method 100 according to the invention. The method 100 for determining orthogonal slice image data sets of a tomosynthesis recording of an examination region, in particular, a breast, has the steps of recording 101, reconstructing 102, selecting 103, masking 104 and determining 105. In the step of recording 101, a tomosynthesis recording is made. In the step of reconstructing 102, a plurality of first slice image data sets is reconstructed in a first plane based upon the tomosynthesis recording. In the step of selecting 103, a first slice image data set is selected from the plurality of first slice image data sets. In the step of marking 104, a microcalcification or a region of interest is marked with a punctiform marking in the selected first slice image data set. In the step of determining 105, a second slice image data set is determined in a second plane orthogonal to the first plane and a third slice image data set is determined in a plane orthogonal to the first plane and the second plane, wherein the point of intersection of the first plane, the second plane and the third plane includes the punctiform marking. The method can further comprise a step of displaying, in particular, of the selected first, second and third slice image data set.

In a step of detecting 106, the at least one microcalcification can also be detected automatically or possibly manually in the first slice image data sets. In a step of cluster analysis 107, given a plurality of detected microcalcifications, an automatic cluster analysis 107 can be carried out.

The second slice image data set and the third slice image data set have exclusively the attenuation information of the at least one microcalcification. Alternatively, the second slice image data set and the third slice image data set have exclusively the attenuation information of the glandular tissue. Alternatively, the second slice image data set and the third slice image data set can have the attenuation information of the glandular tissue and of the at least one microcalcification. The first slice image data set preferably has the entire attenuation information. The marked microcalcification is preferably emphasized in the first, second and third slice image data set. In one embodiment, the second and third slice image data set can have a maximum slice thickness of 4 cm.

In an optional step of marking 108 a biopsy region, a biopsy region can be marked in the first, second and/or third slice image data set. In an optional step of virtual overlaying 109, a model of a selected biopsy needle with a removal opening can be displayed at least in the first slice image data set in the marked biopsy region. In an optional step of checking 110, a message can be output if the selected biopsy needle captures the marked biopsy region incompletely and/or, for the marked biopsy region, a proposal of a suitable biopsy needle and/or of a biopsy angle is output. In an optional step of calculating 111, a trajectory for automatic biopsy control of the biopsy needle can be calculated.

Figure 2:
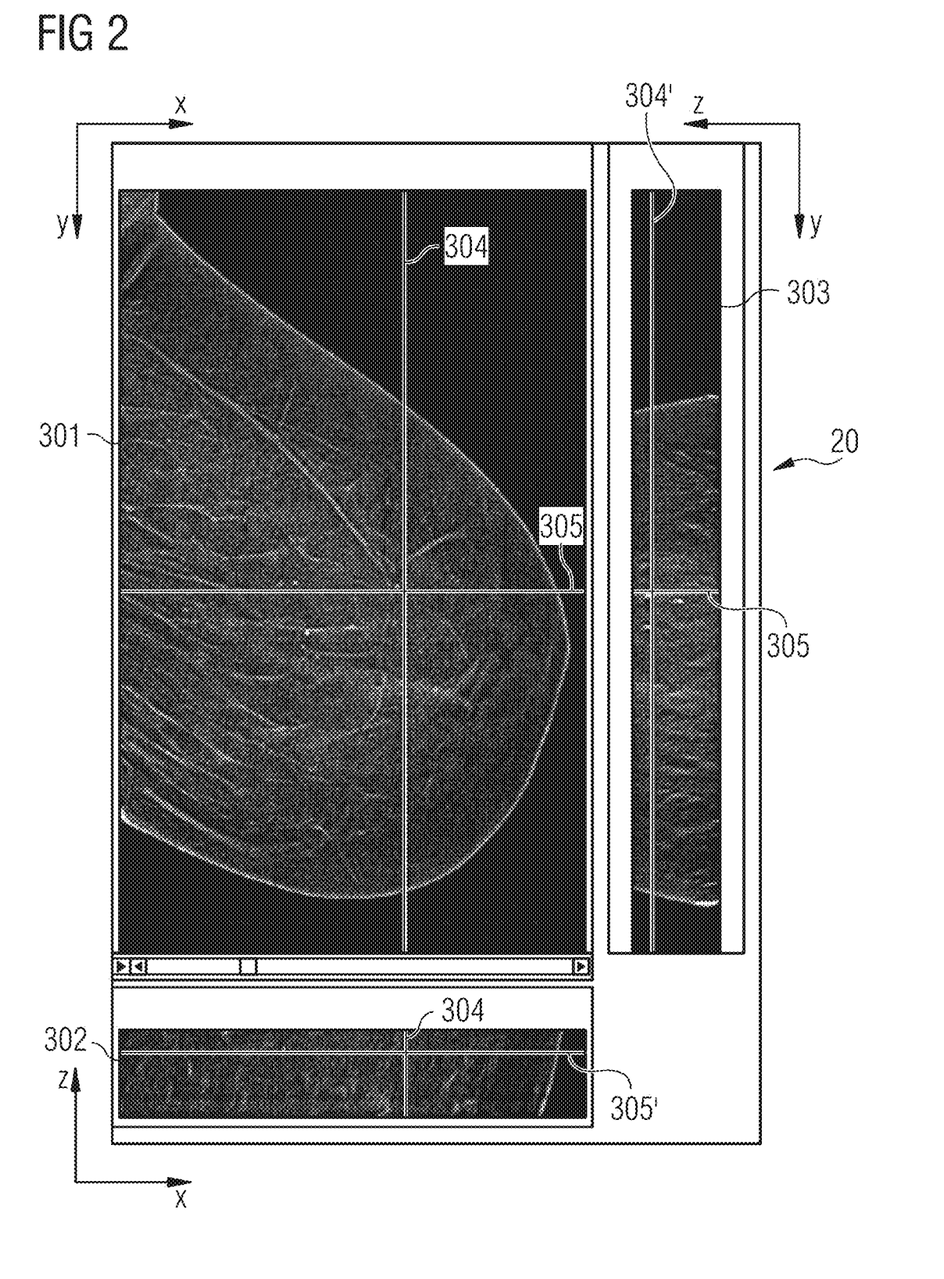
FIG. 2 shows a schematic representation of the representation according to an embodiment of the invention on a display unit of a mammography system.

FIG. 2 shows an example embodiment of the representation according to the invention on a display unit of a mammography system. The display unit can be the output unit 20. In a main region, the selected first slice image data set 301 is displayed in an xy-plane. A first virtual marking line 304 and a second horizontal marking line 305 intersect and the punctiform marking lies at this intersection point. In an adjacent region, for example, arranged therebelow with the same x-scale, the second slice image data set 302 is displayed in an xz-plane. The first marking line 304 is displayed at the same x-position as in the selected first slice image data set 301. The second marking line 305' is displayed at the z-position of the selected first slice image data set 301. In an adjacent region, for example, arranged beside the main region with the same y-scale, the third slice image data set 303 is displayed in a yz-plane. The second marking line 305 is displayed at the same y-position as in the selected first slice image data set 301. The first marking line 304' is displayed at the z-position of the selected first slice image data set 301. The selected first slice image data set 301, second slice image data set 302 and third slice image data set 303 show microcalcifications which are recognizable as white points, and also the soft tissue or the breast background.

Figure 3:
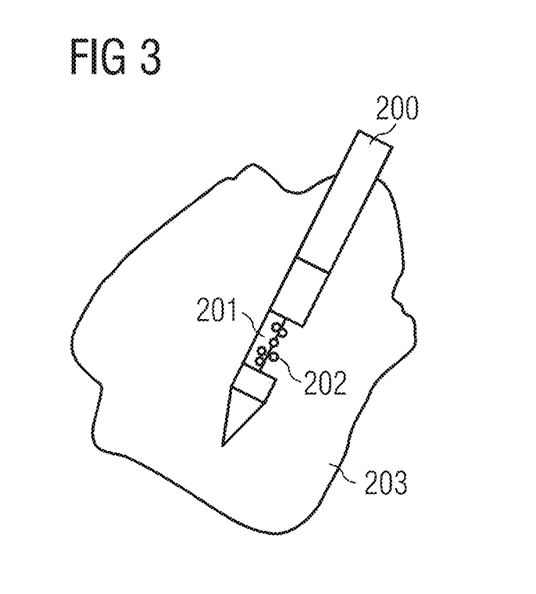
FIG. 3 shows a schematic representation of a virtual overlaying of a biopsy needle in a first slice image data set in a first embodiment.

FIG. 3 shows an example embodiment of a virtual overlaying of a biopsy needle 200 in a first slice image data set in a first embodiment. Both the size of the biopsy needle 200, the size of the notch 201 and also the path or the trajectory are optimally matched to the biopsy region with the microcalcifications 202 in a tissue 203.

Figure 4:
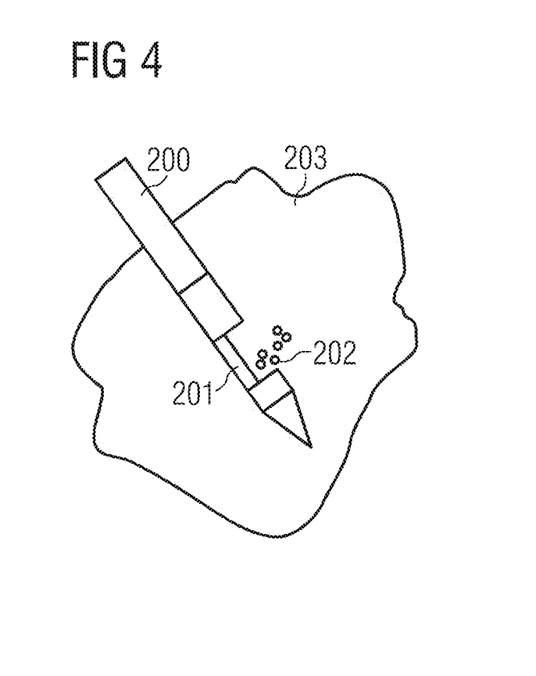
FIG. 4 shows a schematic representation of a virtual overlaying of a biopsy needle in a first slice image data set in a second embodiment.

FIG. 4 shows an example embodiment of a virtual overlaying of a biopsy needle 200 in a first slice image data set in a second embodiment. The path or the trajectory or the access route are not ideal. The needle size of the biopsy needle 200 and the size of the notch 201 are not sufficient for the extraction of the entire cluster having the microcalcifications 202.

Figure 5:
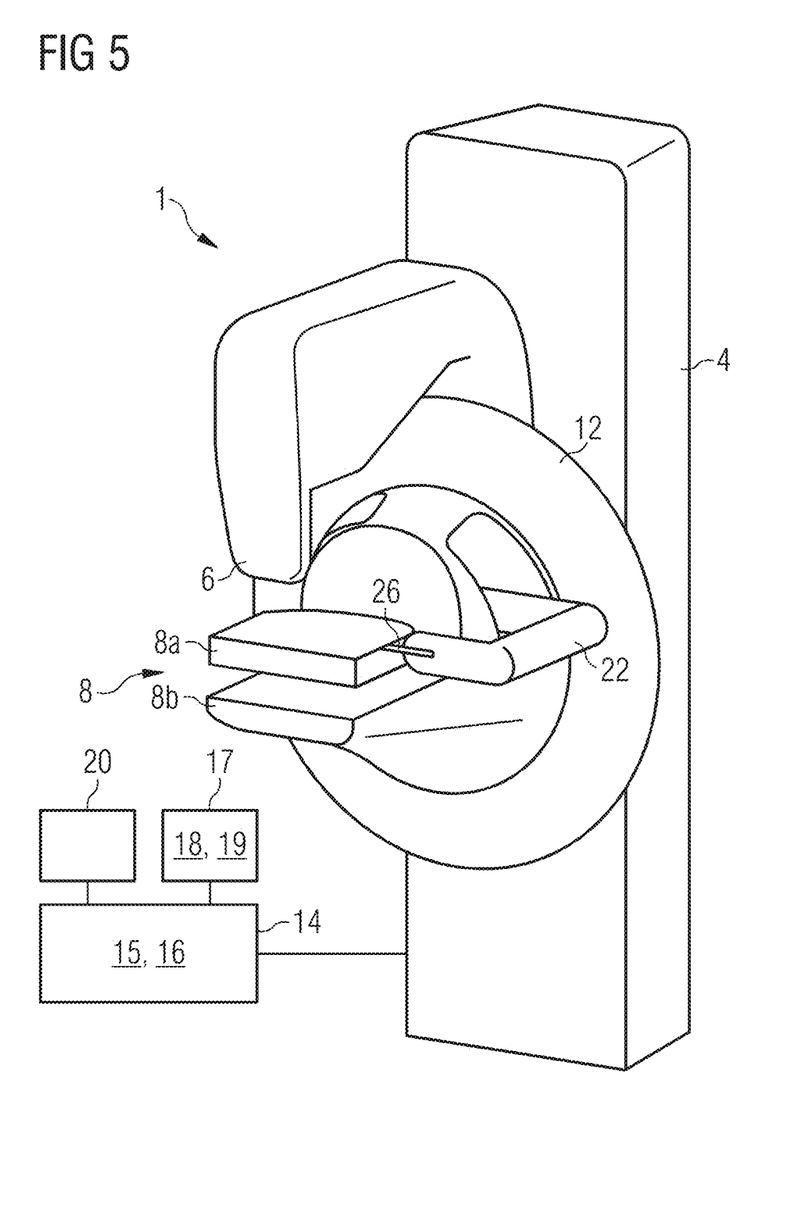
FIG. 5 shows a schematic representation of a mammography system according to an embodiment of the invention.

FIG. 5 shows an example embodiment of a mammography system 1 according to the invention. The mammography system 1 comprises a stand unit 4 with an X-ray arm which is rotatable in a pre-determined angular range and an X-ray source 6 arranged thereon. Further arranged on the stand unit 4 is a rotation unit 12 on which both the compression unit 8 and also the biopsy unit 22 are rotatable for setting a compression direction or a biopsy path. The compression unit 8 comprises the compression element 8a and the X-ray detector 8b between which the breast is positioned and compressed for recording. A biopsy needle 26 is arranged on the biopsy unit 22. The mammography system comprises a computer unit 14 with a reconstruction unit 15 and a determining unit 16. An input unit 17 which comprises the selecting unit 18 and the marking unit 19 is connected to the computer unit. The input unit 17 can comprise, in particular, a user interface, for example, a mouse or a touch user interface. Further connected to the computer unit 14 is the output unit 20, which can comprise a display unit and/or a screen.

Although the invention has been described in detail with the preferred example embodiment, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining orthogonal slice image data sets of a tomosynthesis recording of an examination region, the method comprising:
   recording a tomosynthesis recording and reconstructing a plurality of first slice image data sets in a first plane based upon the tomosynthesis recording;
   selecting a first slice image data set from the plurality of first slice image data sets;
   marking a microcalcification or a region of interest with a punctiform marking in the first slice image data set selected; and
   determining, from a second slice image data set in a second plane orthogonal to the first plane, and from a third slice image data set in a third plane orthogonal to the first plane and the second plane, wherein a point of intersection of the first plane, the second plane and the third plane includes the punctiform marking.

2. The method of claim 1, wherein at least one microcalcification is automatically detected.

3. The method of claim 1, wherein upon the at least one microcalcification detected including a plurality of detected microcalcifications, an automatic cluster analysis is carried out.

4. The method of claim 1, wherein the second slice image data set and the third slice image data set exclusively include attenuation information of the at least one microcalcification.

5. The method of claim 1, wherein the second slice image data set and the third slice image data set exclusively include attenuation information of a glandular tissue or attenuation information of the glandular tissue and the at least one microcalcification.

6. The method of claim 1, wherein the first slice image data set includes entirely all attenuation information.

7. The method of claim 1, wherein the microcalcification marked is emphasized in the first slice image data set, the second slice image data set and the third slice image data set.

8. The method of claim 1, wherein the second slice image data set and the third slice image data set have a maximum slice thickness of 4 cm.

9. The method of claim 1, wherein a biopsy region is marked in at least one of the first slice image data set, the second slice image data set and the third slice image data set.

10. The method of claim 9, wherein a virtual overlaying of a model of a selected biopsy needle, with a removal opening at least in the first slice image data set, is displayed in the biopsy region marked.

11. The method of claim 9, wherein at least one of
a message is output upon the selected biopsy needle incompletely capturing the biopsy region marked and,
a proposal is output for the biopsy region marked, of at least one of a suitable biopsy needle and a biopsy angle.

12. The method of claim 9, wherein a trajectory for automatic biopsy control of the biopsy needle is calculated.

13. A mammography system, comprising:
means for recording a tomosynthesis recording and reconstructing a plurality of first slice image data sets in a first plane based upon the tomosynthesis recording;
means for selecting a first slice image data set from the plurality of first slice image data sets;
means for marking a microcalcification or a region of interest with a punctiform marking in the first slice image data set selected; and
means for determining, from a second slice image data set in a second plane orthogonal to the first plane, and from a third slice image data set in a third plane orthogonal to the first plane and the second plane, wherein a point of intersection of the first plane, the second plane and the third plane includes the punctiform marking.

14. A non-transitory computer program product storing a computer program, directly loadable into a memory apparatus of a control apparatus of a mammography system, including program portions to carry out the method of claim 1 when the computer program is executed in the control apparatus of the mammography system.

15. A non-transitory computer-readable medium storing program portions, configured to be read in and executed by a computer unit, to carry out the method of claim 1 when the program portions are executed by the mammography system.

16. The method of claim 2, wherein the at least one microcalcification detected includes a plurality of detected microcalcifications, wherein the plurality of detected microcalcifications are automatically detected.

17. The method of claim 2, wherein the first slice image data set includes entirely all attenuation information.

18. The method of claim 2, wherein the microcalcification marked is emphasized in the first slice image data set, the second slice image data set and the third slice image data set.

19. The method of claim 2, wherein the second slice image data set and the third slice image data set have a maximum slice thickness of 4 cm.

20. The method of claim 2, wherein a biopsy region is marked in at least one of the first slice image data set, the second slice image data set and the third slice image data set.

* * * * *